United States Patent
Snel et al.

(10) Patent No.: US 10,215,552 B2
(45) Date of Patent: Feb. 26, 2019

(54) OPTICAL COHERENCE TOMOGRAPHY MICROSCOPY APPARATUS AND METHOD FOR DETECTING A THREE-DIMENSIONAL IMAGE OF AN OBJECT

(71) Applicant: Nederlandse Organisatie voor toegepast-natuurwetenschappelijk onderzoek TNO, 's-Gravenhage (NL)

(72) Inventors: Robert Snel, 's-Gravenhage (NL); Wouter Andries Jonker, 's-Gravenhage (NL); Thomas Liebig, 's-Gravenhage (NL); Jasper Winters, 's-Gravenhage (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 111 days.

(21) Appl. No.: 15/321,467

(22) PCT Filed: Jun. 30, 2015

(86) PCT No.: PCT/NL2015/050476
§ 371 (c)(1),
(2) Date: Dec. 22, 2016

(87) PCT Pub. No.: WO2016/003274
PCT Pub. Date: Jan. 7, 2016

(65) Prior Publication Data
US 2017/0199023 A1    Jul. 13, 2017

(30) Foreign Application Priority Data
Jul. 1, 2014  (EP) .................................. 14175212

(51) Int. Cl.
*G01B 9/02* (2006.01)
*A61B 5/00* (2006.01)

(52) U.S. Cl.
CPC ........ *G01B 9/02091* (2013.01); *A61B 5/0066* (2013.01); *G01B 9/0201* (2013.01); *G01B 9/02071* (2013.01); *G01B 2290/60* (2013.01)

(58) Field of Classification Search
CPC ... G01B 9/02091; A61B 3/102; A61B 5/0033; A61B 5/0073; A61B 2019/5234;
(Continued)

(56) References Cited

U.S. PATENT DOCUMENTS 5,659,392 A    8/1997  Marcus et al.
5,994,690 A *  11/1999 Kulkarni ............. A61B 5/7257
                                              250/216
(Continued)

FOREIGN PATENT DOCUMENTS

DE    102005031216 A1    1/2007

OTHER PUBLICATIONS

Sep. 14, 2015—International Search Report and Written Opinion of PCT/NL2015/050476.
Dec. 12, 2014—European Search Report of EP 14175212.1.

*Primary Examiner* — Michael P LaPage
(74) *Attorney, Agent, or Firm* — Banner & Witcoff, Ltd.

(57) ABSTRACT

An optical coherence tomography microscopy apparatus (1) is presented for detecting a three-dimensional image of an optically translucent or reflective sample object (OS), the apparatus comprising an interferometric optical setup including a photo sensor unit (20). A sense signal Si from the photo sensor unit (20) is detected using a detection reference signal. The detection reference signal is derived from a signal indicative for a relative displacement of the sample object (OS) with respect to a reference object.

24 Claims, 8 Drawing Sheets

(58) Field of Classification Search
CPC .......... A61B 2090/3735; A61B 5/0066; G06T 2207/101019
See application file for complete search history.

(56) References Cited

U.S. PATENT DOCUMENTS

| | | | |
|---|---|---|---|
| 6,006,128 A | | 12/1999 | Izatt et al. |
| 6,191,862 B1* | | 2/2001 | Swanson ............ G01B 11/2441 356/479 |
| 2007/0076217 A1* | | 4/2007 | Baker .................. A61B 3/1005 356/498 |
| 2008/0285043 A1* | | 11/2008 | Fercher .................. A61B 3/102 356/451 |
| 2009/0268213 A1 | | 10/2009 | Blalock et al. |
| 2010/0309479 A1 | | 12/2010 | Yamauchi et al. |
| 2011/0235056 A1 | | 9/2011 | Matsudo et al. |
| 2014/0221827 A1* | | 8/2014 | Motaghiannezam ........................ G01N 21/4795 600/425 |
| 2018/0055355 A1* | | 3/2018 | Sarunic ................ A61B 3/1233 |

\* cited by examiner

OPTICAL COHERENCE TOMOGRAPHY MICROSCOPY APPARATUS AND METHOD FOR DETECTING A THREE-DIMENSIONAL IMAGE OF AN OBJECT

CROSS-REFERENCE TO RELATED APPLICATIONS

This application is a U.S. National Stage application under 35 U.S.C. § 371 of International Application PCT/NL2015/050476 (published as WO 2016/003274 A1), filed Jun. 30, 2015, which claims the benefit of priority to EP 14175212.1, filed Jul. 1, 2014. Benefit of the filing date of each of these prior applications is hereby claimed. Each of these prior applications is hereby incorporated by reference in its entirety.

BACKGROUND OF THE INVENTION

Field of the Invention

The present invention relates to an optical coherence tomography microscopy apparatus.

The present invention further relates to an optical coherence tomography microscopy method.

Related Art

EP 1 892 501 discloses an interferometric optical setup that uses a low temporal coherence of a tunable broad-band light source to resolve the axial dimension. The set-up includes a single opto-mechanical or electronic scanning mechanism for accessing different object depths, and a two-dimensional photo sensor device capable of demodulating the temporally or spatially modulated scanning signals to reconstruct the object's full volume.

The cited European patent does not specify how the photo sensor device demodulates the scanning signals. Standard demodulation techniques are known that involve band-pass filtering, rectifying and low-pass filtering the scanning signals. Generally this requires large RC constants, which are not compatible for implementation in CMOS processes.

It is noted that U.S. Pat. No. 6,006,128A discloses a method for generating a velocity-indicating, tomographic image of a sample in an optical coherence tomography system. The method includes a first step of (a) acquiring cross-correlation data from an interferometer. The cross-correlation data is used to generate a grayscale image indicative of a depth-dependent positions of scatterers in the sample. The cross-correlation data is processed to produce a velocity value and location of a moving scatterer in the sample and colors are assigned to the velocity value. The data acquisition system also utilizes a calibration interferometer for providing a calibration of a reference arm position during interferogram acquisition. The system disclosed therein is not intended to scan a surface profile, but serves to measure velocity by means of detecting a frequency shift (the dopplershift) of a reference mirror with respect to the object under surveillance. This necessitates split light paths.

It is further noted that US2009/268213A1 discloses an apparatus for measuring the axial length of a human eye. The apparatus comprises a low coherence light source; a beam splitter; a fast displacement module for rapidly varying the path length within a reference arm of an interferometer. The apparatus further includes a laser directing a laser beam that is co-propagating with light from the low coherence light source into the displacement module. Paragraph [0034] states that "the computer 124 receives a signal from interferometer 134, which enables monitoring of the changes of the path length of reference arm 120 with a sub-micrometer precision. US2009/268213A1 does not disclose how this signal is used by the computer. However, in the same paragraph [0034] it specifies that: "The wavelength of the laser should be different from the spectrum of the low coherence light source 112."

It is still further noted that US2010/309479A1 discloses an interference measuring device that comprises a displacement detecting unit, a piezoelectric actuator and a drive unit, a mirror, a stage, a drive unit, and a control unit. According to a result of optical path length difference detection by the displacement detecting unit the control unit controls optical path length difference adjusting operations by the piezoelectric actuator to sequentially set the optical path length difference to one of a plurality of target values.

It is still further noted that U.S. Pat. No. 5,659,392A discloses an associated dual interferometric measurement apparatus for determining a physical property of an object, such as thickness, group index of refraction, and distance to a surface. The apparatus includes a non-coherent light interferometer and a coherent light interferometer in association so as to share a variable optical path delay element. Thickness measurements can be made, for example, of solids, liquids, liquids moving along a horizontal plane, or liquids flowing down a plane. Thickness measurements of multiple layers can be made. The analog output of photodetector indicative for the low-coherence radiation interference pattern is amplified and filtered by an electronic module, and digitized by utilizing the coherent light interferometer data acquisition trigger pulses by processing electronics that is capacitively coupled to a further photodetector.

Known optical coherence tomography microscopy apparatuses are typically intended for use in well-controlled circumstances, such as in a laboratory environment, but are unsuitable for general application where vibrations in the environment and other disturbances cannot be avoided. Accordingly, another approach is desired that is more generally applicable in such environments.

SUMMARY OF THE INVENTION

According to a first aspect of the present invention an improved optical coherence tomography microscopy apparatus is provided as claimed in claim 1.

In summary, the optical coherence tomography microscopy apparatus for detecting a three-dimensional image of an optically translucent or reflective sample object an interferometric optical setup including a photo sensor unit and a light source, which may comprise one or more light emitting elements.

Temporal infringement patterns resulting from differences in path length of a first path including the sample object and a second path including a reference object are sensed. A sense signal from the photo sensor unit is detected using a detection reference signal that is derived from a measurement of actual changes in said path length difference. Accordingly, a period of the reference signal Sr corresponds to a predetermined change in path length difference. In addition a period of the reference signal Sr corresponds closely to a fraction $\frac{1}{2}N$ of the period of the sense signal Si, wherein N is a positive integer. For example N=2, so that the period of the reference signal Sr corresponds closely to a quarter of the period of the sense signal Si. Hence, the phase of the reference signal indicates the actual displacement, even if this deviates from an expected displacement, for example due to vibrations induced by the environment. Therewith the exact point in time where the sense signal is sampled is adapted in accordance with the actual displacement. Therewith a more reliable demodulation of the sense signal is achieved.

It is noted that this is not disclosed by the cited prior art. For example according to U.S. Pat. No. 6,006,128 the digital clock source signal for clocking (triggering) the analog to digital converters is generated by a clock generator. This document pertains to measure particle velocities, instead of measuring a surface profile. The digital clock source signal that is used to sample the analog to digital converters merely need to adapt to fluctuations in the reference mirror 36 translation velocity. See col. 15, lines 29-33.

US2009/268213A1 does not specify how the changes of the path length of reference arm therein are measured. However, in paragraph [0034] it is disclosed that the wavelength of the laser should be different from the spectrum of the low coherence light source. Therewith this cited document points away from the requirement that a period of the reference signal Sr corresponds closely to a fraction ½N of the period of the sense signal Si.

As indicated above US2010/309479A1 discloses that the displacement detection signal is used to control the actuator that changes the path length. Although this provides for some compensation against vibrations, this is less effective than using the displacement detection signal for sampling the sense signal. The reason is that a feedback loop for controlling the actuator will inevitably have a certain phase deviation, due to the mass of the components that are controlled by the actuator. The present invention avoids this in that the displacement information as provided by the displacement sensor is used to provide for a compensation in the way the sense signal is processed. This obviates a separate vibration compensation loop in the actuator therewith avoiding a delay due to mechanical inertia of components.

As also indicated above U.S. Pat. No. 5,659,392A, col. 15, lines 42-46 discloses a capacitive coupling of the photodetector to the processing electronics that generate the acquisition trigger pulses. This implies that the phase of the signal received by the processing electronics no longer corresponds to the actual displacement. Not only does the capacitor result in a phase shift, but this phase shift depends on the frequency of the variations in the displacement including the frequency of the vibrations, which are not exactly known.

Various options are possible to measure changes in said path length difference, for example using an ruler-encoder position detector.

In this embodiment the ruler-encoder type of displacement sensor is used to generate the detection reference signal with a period (reference period) corresponding to a predetermined change in path length difference that corresponds closely to a fraction ½N of the period of the sense signal, wherein N is a positive integer.

This may be achieved in that the specification of the ruler encoder is adapted to a specification of the light source to provide the reference signal to sample the sense signal with said reference period corresponding to the predetermined change in path length difference that corresponds closely to said fraction.

In an embodiment, the ruler-encoder is arranged to provide a first output signal indicative for a sine function of the displacement and a second output signal indicative for a cosine function of the displacement, which first and second output signal in combination indicate a phase that linearly varies with the displacement, the apparatus further being provided with a linear interpolator that outputs the reference signal as a signal having a phase that is a multiplication factor times the phase of the signal indicated by the first and the second output signal, said multiplication factor being specified in accordance with the specification of the light source to provide the reference signal to sample the sense signal.

In an embodiment the detection reference signal is obtained by measuring interference in a relative narrow bandwidth as compared to a bandwidth of the radiation used to derive the sense signal.

In an embodiment of the optical coherence tomography microscopy apparatus according to the first aspect of the invention the demodulator comprises a detector using a detection reference signal related to a carrier frequency of the sense signal, and a reference signal generator to generate the detection reference signal.

The reference signal generator includes a photo sensor to measure a temporal change in interference in a sensing bandwidth narrower than said emission bandwidth, said interference occurring between a third sub-beam being directed along a third optical path including the sample object and a fourth sub-beam directed along a fourth optical path including the reference object and originating from a common light source. A path length difference between the third and the fourth optical path changes corresponding to said changing difference between the path length of the first optical path and the path length of the second optical path.

The measurement of interference using a sensing bandwidth that is substantially narrower that the emission bandwidth results in an auxiliary sense signal that has a relatively constant amplitude over a relatively long variation of the path difference, but that has a carrier frequency that is closely related to the carrier frequency of the sense signal resulting from interference in the emission bandwidth. Therewith an accurate detection of the sense signal is achieved.

According to a second aspect of the present invention an improved optical coherence tomography microscopy method is provided as claimed in claim 18.

BRIEF DESCRIPTION OF THE DRAWINGS

These and other aspects are described in more detail with reference to the drawing. Therein.

DETAILED DESCRIPTION OF EMBODIMENTS

Like reference symbols in the various drawings indicate like elements unless otherwise indicated.

In the following detailed description numerous specific details are set forth in order to provide a thorough understanding of the present invention. However, it will be understood by one skilled in the art that the present invention may be practiced without these specific details. In other instances, well known methods, procedures, and components have not been described in detail so as not to obscure aspects of the present invention.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. All publications, patent applications, patents, and other references mentioned herein are incorporated by reference in their entirety. In case of conflict, the present specification, including definitions, will control. In addition, the materials, methods, and examples are illustrative only and not intended to be limiting.

It will be understood that, although the terms first, second, third etc. may be used herein to describe various elements (e.g. multipliers or other components), items (e.g. optical path, (sub-) beam, multiplication signal), or phenomena (interference) these elements, items and/or phenomena should not be limited by these terms. These terms are only used to distinguish one element, item or phenomenon from another element, item or phenomenon. Thus, a first element, item or phenomenon discussed below could be termed a second element, item or phenomenon without departing from the teachings of the present invention.

Figure 1:
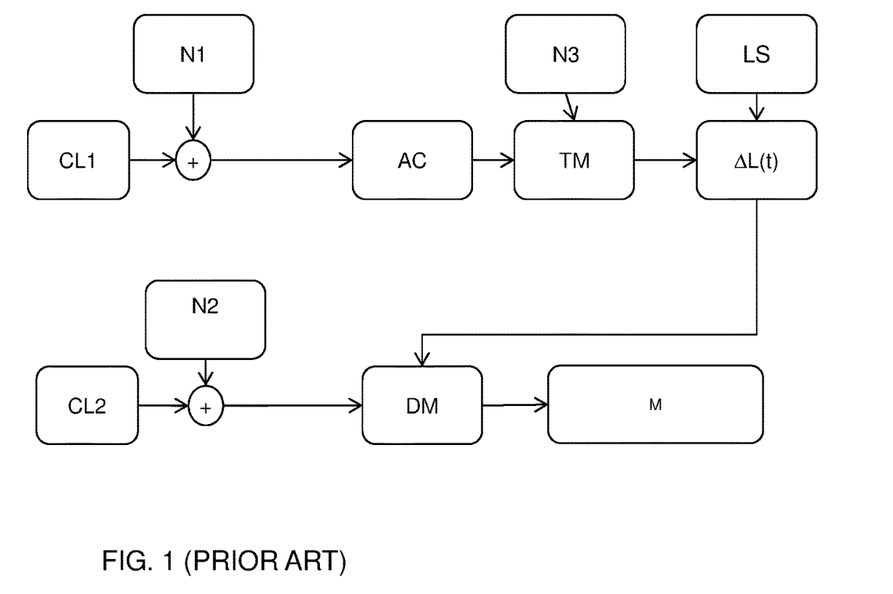
FIG. 1 schematically shows an optical coherence tomography microscopy apparatus according to prior art, FIG. 2 schematically shows an optical coherence tomography microscopy apparatus according to a first aspect of the invention.

FIG. 1 schematically shows operation of a prior art optical coherence tomography microscopy apparatus. The apparatus includes a coherent light source LS and a photo sensor that senses temporal interference patterns.

The temporal interference patterns result from an interference in between a first and a second sub-beam impingent on a sensing region, and that are split off from beam emitted by the light source. The first sub-beam is directed along a first optical path extending from the light source to the sensing region via a sample object and the second sub-beam is directed along a second optical path extending from the light source to the sensing region via a reference object. A difference in length (path length difference) between the first optical path and the second optical path is varied as a function of time.

A first clock CL1 is used to control an actuator AC coupled to a mechanical system TM that provides for a displacement, in order to change the path length difference as a function of time ($\Delta L(t)$). A signal issued by the photo sensor is provided to a detector DM that provides measurement results M. The detector DM uses a trigger signal issued by a clock CL2. Ideally, the clock signal is a reliable indication for the displacement of the sample object relative to the reference object. However, in practice the clocks CL1, CL2 may be subject to jitter N1, N2 and even worse vibrations in the environment, indicated as noise N3, may cause serious deviations between the actual displacement and the desired displacement. As a result the prior art optical coherence tomography microscopy apparatus, although useful in laboratory environments, with well controlled circumstances, is unsuitable for use in industrial environments, where vibrations would prevent it from functioning properly.

Figure 2:
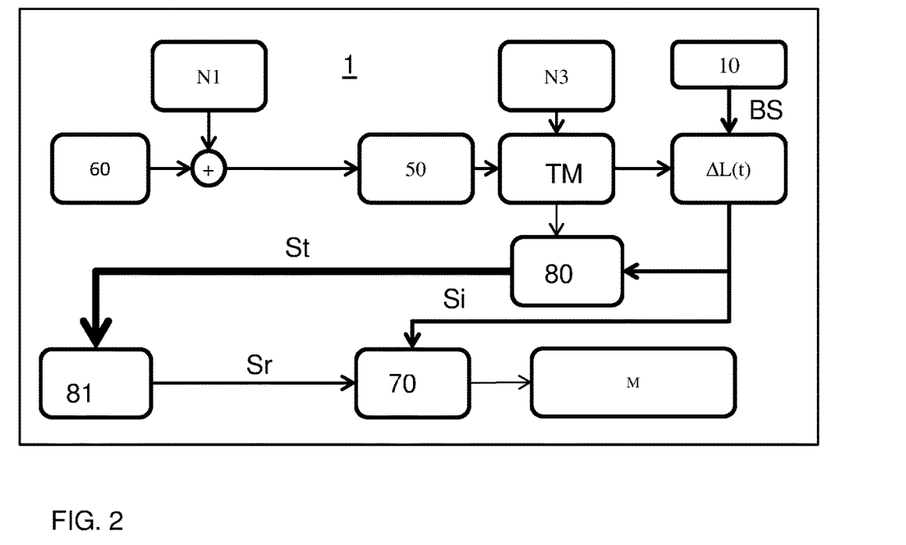

FIG. 2 schematically shows an optical coherence tomography microscopy apparatus 1 according to the first aspect of the present invention. The apparatus is configured for detecting a three-dimensional image of an optically translucent or reflective sample object. The apparatus comprises an interferometric optical setup that includes a light source 10 that comprises one or more light emitting elements to emit a beam of light BS having an emission bandwidth. As described above, temporal interference patterns resulting from a time-varying path length difference ($\Delta L$) are measured. Examples of such optical arrangements for this purpose are described in more detail in the sequel. The apparatus includes a displacement unit 50 controlled by a controller 50 that varies the path length difference ($\Delta L$) resulting in temporal interference patterns. The displacement unit may for example displace the sample object or the reference object or both. A sense signal Si indicative for said temporal interference patterns is provided as input signal to a detector 70, tot generate a measurement signal M.

The apparatus according to the present invention further includes a displacement sensor 80 to generate a displacement signal St indicative for the change in path length difference and a reference signal generator 81 to generate a detection reference signal Sr from the displacement signal St. The demodulator comprises a detector 70 that uses the detection reference signal Sr.

Figure 3:
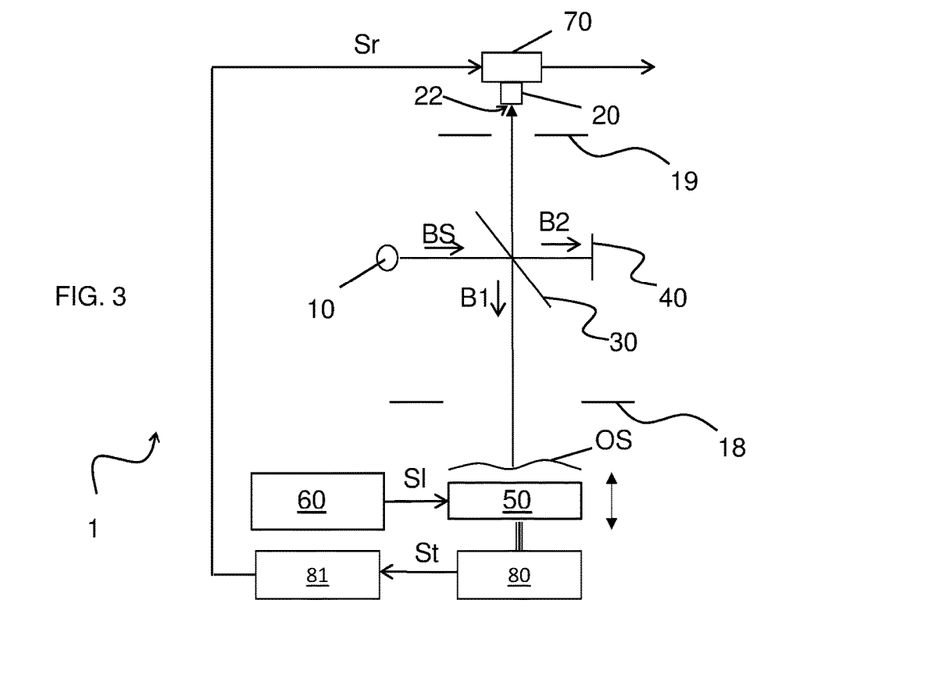
FIG. 3 shows an optical coherence tomography microscopy apparatus according to an embodiment of the first aspect of the invention in more detail.

As indicated in FIG. 2, noise N1 may perturb the actuator control signal provided by controller 60. Also mechanical noise N3, for example from neighboring machinery will have the effect that the actual path length difference variations deviate from the path length difference variations that were scheduled by the controller 60. However, in the apparatus according to the invention the displacement sensor 80 provides the signal St that is indicative for the actual path length difference variations and that is used by the reference signal generator 81 to generate the reference signal. Therewith the detector 70 can more reliably retrieve the measurement results from the sense signal Si, which is perturbed by the same noise factors as the detection reference signal Sr, Several options are possible for the displacement sensor 80. FIG. 3 shows a first embodiment of an optical coherence tomography microscopy apparatus 1 for detecting a three-dimensional image of an optically translucent or reflective sample object.

The apparatus comprises an interferometric optical setup that includes a light source 10 for instance a super luminescent diode (SLD) to emit a beam of light BS having an emission bandwidth. By way of example a LED, for instance an SLD, is used having a central wavelength of 635 nm, and an emission bandwidth of for example 100 nm. As a result of the relatively large emission bandwidth, the coherence length is relatively short. Therewith it can be determined with a relatively high accuracy whether the path length difference is close to 0.

The interferometric optical setup further includes a photo sensor unit 20. The photo sensor unit 20 has at least one photo sensor able to sense a light intensity in a sensing region 22 and to generate a sense signal indicative for said light intensity. Typically the photo sensor unit 20 is a photo sensor array comprising a plurality of photo sensors. A detector 70 is provided for deriving a measurement result from the sense signal, using a detection reference signal Sr. In an embodiment wherein the photo sensor unit 20 is a photo sensor array comprising a plurality of photo sensors, each photo sensor in the array may have its own detector. Such a photo sensor array may be provided as an integrated circuit comprising a plurality of units each having a photo sensor and a corresponding detector. The sensed light intensity is dependent on interference between a first and a second sub-beam B1, B2 impingent on and overlapping in the sensing region. These sub-beams B1, B2 are split off from the emitted beam BS by beam splitter 30. The first sub-beam B1 is directed along a first optical path that extends from the light source 10, via the sample object, here a reflective sample object OS to the sensing region 22. The second sub-beam B2 is directed along a second optical path that extends from the light source 10, via the reference object 40, here also a reflective object to the sensing region 22.

A displacement unit 50, is provided to change a difference in path length between the first optical path and the second optical path. This causes a modulation in the light intensity sensed by the photo sensor unit 20. In the embodiment shown the displacement unit 50 displaces the sample object OS, but in an alternative embodiment a displacement unit may be provided that displaces the reference object 40, or that otherwise changes the path length difference. Typically the path length difference is changed in a constant pace, e.g., however alternatively the speed with which the path length difference is changed may be adapted to sensed features.

In the embodiment shown the displacement unit 50 is controlled by a controller 60 with control signal Sl. The controller 60 may also control other functions of the apparatus. In this case the displacement unit 50 is mechanically coupled to a displacement sensor 80. In an embodiment the displacement sensor 80 is provided as a ruler encoder, having a markings at a mutual distance of 20 micron and a photo sensor to sense the markings.

In this case the ruler-encoder is arranged to provide a first output signal indicative for a sine function of a detected displacement and a second output signal indicative for a cosine function of the detected displacement, together indicated as signal St. The first and second output signal in combination indicate a phase that linearly varies with the displacement. The apparatus further is provided with a linear interpolator 81 that outputs the reference signal Sr as a signal having a phase that is a multiplication factor times the phase of the signal indicated by the first and the second output signal. The multiplication factor is specified in accordance with the specification of the light source 10 to provide the reference signal to sample the sense signal.

Accordingly, in case the displacement occurs at a constant velocity, the reference signal generator 81 behaves as a frequency multiplier that outputs a reference signal Sr at a frequency that is a predetermined factor higher than the frequency of the signal St. For example the predetermined factor may be 252, so that the frequency of the reference signal is 252 times the frequency of the signal St. Alternatively, a period of the reference signal Sr corresponding to a displacement of 79.365 nm corresponds to $1/252$ of this distance, i.e. approximately 315 nanometer. This is close enough to half the wavelength of the radiation source (317.5 nm). The reference signal Sr therewith is very suitable for detection of the sense signal Si. As not only the frequency of the reference signal is proportional to the velocity of the displacement, but in particular the phase of the reference signal varies linearly with the displacement, the detection signal accurately indicates the actual displacement, even in case the displacement is includes additional variations by noise due to vibrations for example. Instead of processing the signals of the displacement detector with a linear interpolator 81, it may be considered to directly use the displacement detector signals, for example, in case the displacement detector is by itself capable of generating a displacement with a period corresponding to a relatively small displacement.

It will be understood that the specifications of the light source are merely an example. Other light sources as are conventional in optical coherence. tomography microscopy devices may be used for this purpose. Also optical filters may be used to shape the emission spectrum as desired. Likewise the specification of the ruler decoder and/or the frequency multiplier may be adapted to the specification of the selected light source (with optional filter).

Figure 4:
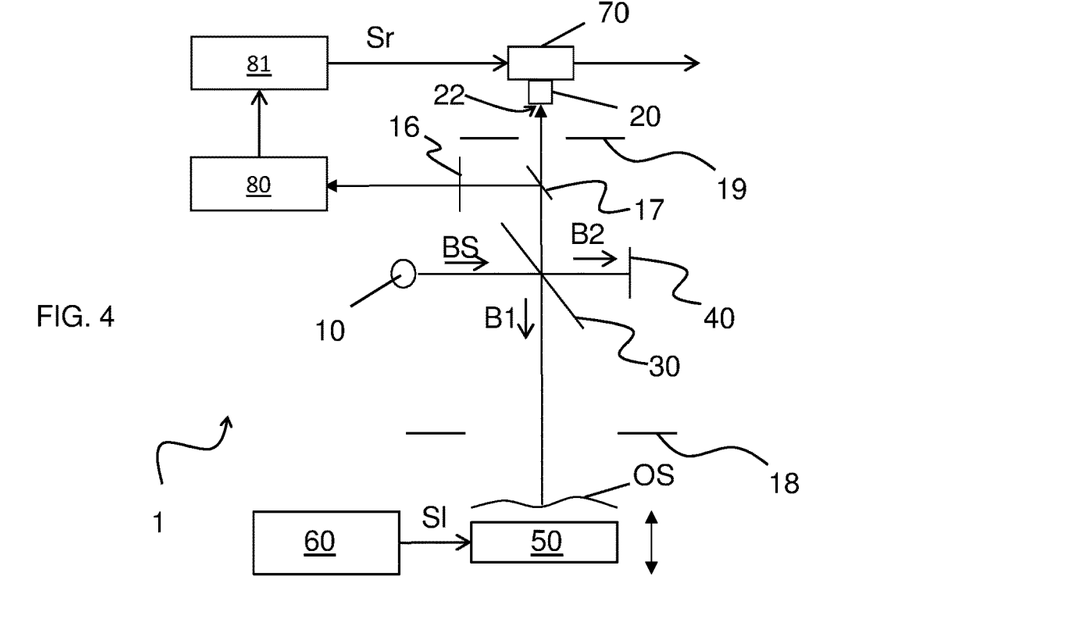
FIG. 4 shows another embodiment of an optical coherence tomography microscopy apparatus according to the present invention.

FIG. 4 shows a second embodiment of an optical coherence tomography microscopy apparatus 1 for detecting a three-dimensional image of an optically translucent or reflective sample object. Parts therein corresponding to those in FIG. 3 are indicated by a corresponding reference.

Figure 4A:
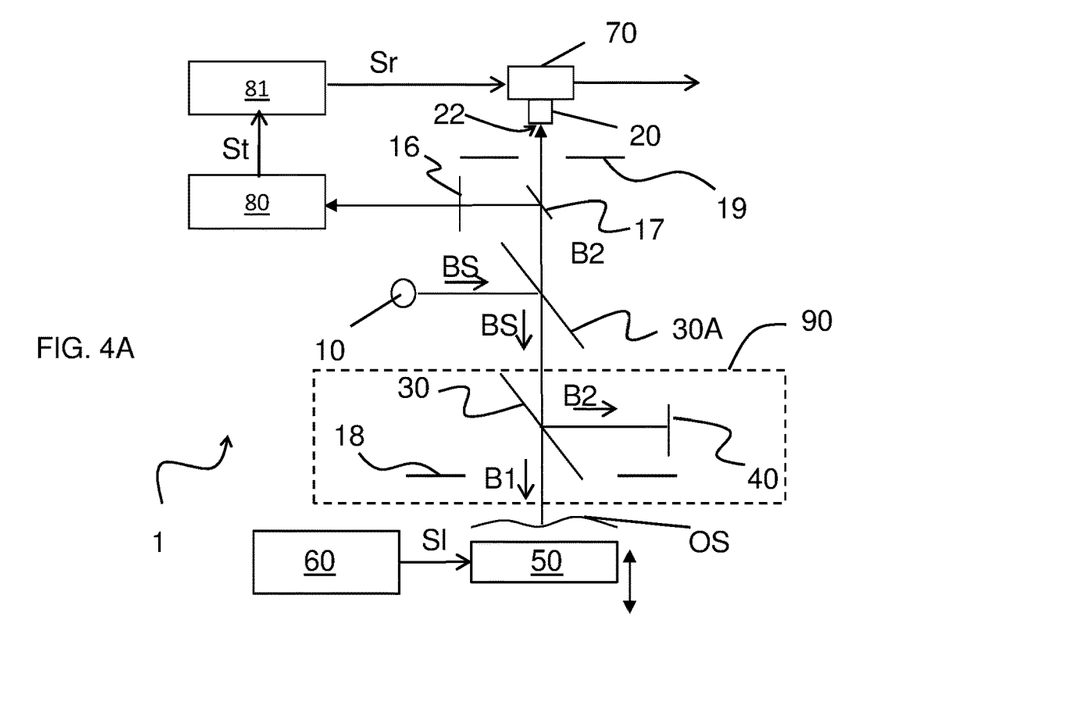
FIG. 4A shows an alternative arrangement of that embodiment.

FIG. 4A shows an alternative arrangement of the first embodiment. Therein a semi-transparent mirror 30A is provided that redirects the emitted beam BS towards the beam splitter 30 that splits the beam BS into beams B1, B2 and also merges the beams reflected by the sample object OS and the reference object 40. In this embodiment the beam splitter 30 may for example be integrated in an objective 90.

In the embodiment of FIG. 4, 4A, the beam-splitter 17 is a semi-transparent mirror that is substantially polarization insensitive. In an alternative embodiment a beam-splitter may be used that is polarization sensitive. In this embodiment the light source 10 may be arranged to emit a first light component in an emission bandwidth having first polarization properties and emit a second light component in a sub-band of the emission bandwidth having second polarization properties. The emitted light BS then is splitted in a first and a second beam B1, B2 that each includes both the light components. However, the polarization sensitive beam-splitter directs the first component, with the first and the second sub-beam towards the photo sensor unit 20 and directs the second component with the third and the fourth sub-beam towards the photo-sensor 80. In that case it is not necessary to use a band filter 16.

In the embodiment of FIG. 4, 4A the paths of the third and the fourth sub-beam substantially correspond to the paths of the first and the second sub-beam. Only the last portion of the third and the fourth sub-beam differs from the last portion of the first and the second sub-beam as a result of the beam-splitter 17. In some embodiments, the paths of the third and the fourth sub-beam may substantially differ from the first and the second sub-beam. In that case it is not necessary to provide an beam-splitter 17 to separate the third and the fourth beam from the first and the second beam. This may be achieved for example by providing the light source 10 with a first and a second light element that emit light into mutually different directions, wherein the first light element emits a first light component in an emission bandwidth and the second light element emits a second light component in a sub-band of the emission bandwidth.

Figure 5:
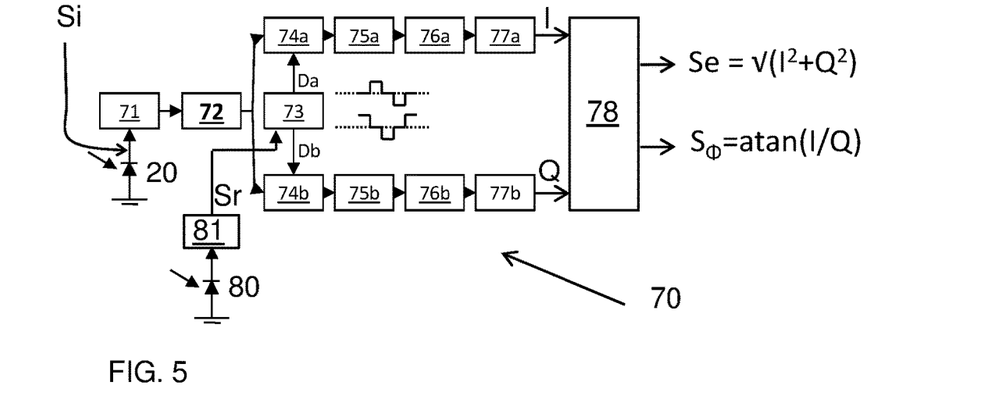
FIG. 5 shows a part for use in an embodiment of an apparatus of the first aspect in more detail.

As shown in more detail in FIG. 5, the demodulator 70 comprises a detector using a detection reference signal Sr corresponding to a carrier frequency of the sense signal Si, and a reference signal generator 80, 81 to generate the detection reference signal. As described above, with reference to FIG. 3, the reference signal generator 81 may generate the reference signal Sr as a function of a displacement sense signal St obtained from a ruler-encoder type of sensor. Alternatively, as described with reference to FIGS. 4 and 4A for example, the reference signal generator may include a photo sensor 80 to measure a temporal change in interference in a sensing bandwidth narrower than said emission bandwidth. As the sensing bandwidth used to generate the detection reference signal Sr is narrower than the emission bandwidth the coherence length is increased. Therewith it is possible to generate the detection reference signal Sr over a large range of path length differences. I.e. it is achieved herewith that the detection reference signal is reliably provided while changing the path length difference in this range.

The photo sensor 80 detects interference between a third and a fourth sub-beam. The third beam is directed along a third optical path that extends from the light source 10 via the beam splitter 30 to the sample object OS, through the beam splitter 30 and via the beam splitter 17 and the optical filter 16 to the photo sensor 80. The fourth sub-beam is directed along a fourth optical path that extends from the light source 10 via the beam splitter 30 to the reference object 40 via the beam splitters 30 and 17 and the optical filter 16 to the photo sensor.

Dependent on the required operational range the optical filter 16 reduces the bandwidth of the third and the fourth beam to a value in the range of about 0.05 nm to about 1 nm.

It is noted that the beam splitter 17 splits incoming light into a fifth beam directed towards the photo sensor unit 20 and a sixth beam directed to the further photo sensor 80.

When the displacement unit 50 displaces the sample object OS, the path length difference between the third and the fourth optical path changes with the same amount as the difference between the path length of the first optical path and the path length of the second optical path. This would also apply if the displacement unit displaces the reference object 40 instead of the sample object.

As indicated above, various options are possible to detect the actual displacement of the sample object OS relative to the reference object 40 for the purpose of generating the reference signal. However, as will be clear from the above, a particularly high measurement accuracy is obtained with an arrangement, wherein the displacement is measured by an additional interferometric path length difference measurement based on infringement in a relatively small bandwidth, i.e. substantially smaller than the emission bandwidth. It is noted that the central wavelength of the photon radiation used to derive the reference signal is preferably substantially equal to the central wavelength of the photon radiation used to derive the sense signal or substantially equal to an integer multiple thereof. This can be achieved by proper optical filtering or by a suitable matching of the radiation sources to each other, if a separate radiation source is used for the purpose of generating the reference signal (See FIG. 7A), or by a combination of both measures. If the central wavelength of the photon radiation used to derive the reference signal deviates from the central wavelength of the photon radiation used to derive the sense signal or an integer multiple thereof, the reference signal generator 81 may be provided with a frequency controller that compensates for these deviations, for example using a phase locked loop that having a predetermined ratio between the frequency of its output signal and its input signal, the output signal the input signal further having linear phase relationship.

Figure 6:
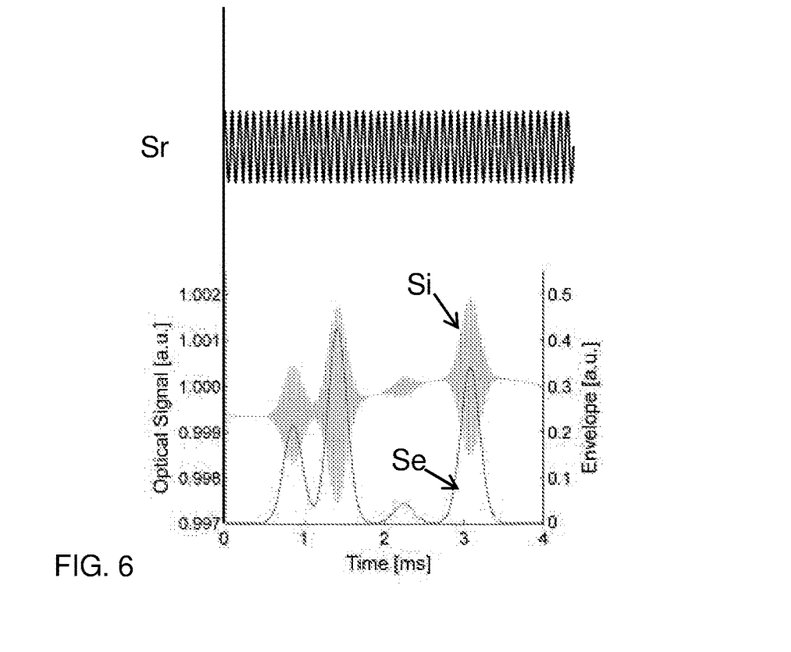
FIG. 6 shows various signals occurring in this part.

The demodulator of FIG. 5 is now described in more detail, also with reference to FIG. 6. As a result of the changing path length difference, a temporally changing interference signal Sr is detected by photo sensor 80 and circuitry 81. If the translation induced by displacement unit 50 is uniform, the interference signal Sr is a sinusoid as shown in the upper half of FIG. 6.

A detection signal generator part 73 generates a pair of detection signals Da, Db that are mutually out of phase. The detection signals Da, Db may likewise be sinusoids. Alternatively an other waveform may be used for detection, e.g. a blockwave. This may simplify the detection.

In the embodiment shown the sense signal Si, as illustrated in FIG. 6, received from the photo sensor unit 20 is preprocessed by a preprocessor 71. The preprocessor 71 may for example remove background noise and apply other operations to improve the signal quality. The signal is subsequently passed to an integrating amplifier 72, and the integrated signal is provided to a first multiplier 74a that multiplies the integrated signal with detection signal Da and a second multiplier 74b that multiplies the integrated signal with detection signal Db. The product signals obtained from the multiplies 74a, 74b is further processed by a summation part 75a, 75b, a sample and hold part 76a, 76b and a quadrature position encoder 77a, 77b to obtain the I,Q signals. Subsequently the envelope signal Se, see FIG. 3, is calculated by combination unit 78 as:

$$Se = \sqrt{(I^2 + Q^2)}$$

The combination unit 78 further calculates a phase signal $S_\Phi$ with $$S_\Phi = a\tan(I/Q)$$

It is noted that the detection circuit 70 illustrated in and described with reference to FIG. 5 is equally suitable for application in the arrangement of FIG. 3, or generally in any arrangement wherein a reference Sr is provided that is indicative for the actual displacement, i.e. the actual change in path length difference.

In the embodiment shown in FIGS. 4 and 5 a further photo sensor 80 is provided to measure the temporal change in interference in the sensing bandwidth narrower than the emission bandwidth. The further photo sensor 80 is arranged to sense an interference pattern for light within the sensing bandwidth in that the band pass filter 16 is arranged between the beam splitter 17 and the photo sensor 80. An arrangement could be considered wherein a band pass filter is only arranged in one of the third and the fourth optical path. In this case the interference pattern is said sensing bandwidth would still be detectable, but to a lesser extent due to the presence of light outside said sensing bandwidth in the one of the third and the second optical path that does not extend via the band pass filter.

In again an alternative embodiment a further photo sensor 80 is applied that is sensitive only for light in the sensing bandwidth. In that case a separate band pass filter is superfluous.

In the embodiment of FIGS. 4 and 5 the common light source is the light source 10. I.e. the same light source that is used to render the sense signal is also used to render the detection reference signal. As an alternative it could further be considered to use a separate light source for the purpose of rendering the detection reference signal. Such a separate light source may emit light in the relatively small sensing bandwidth to achieve the required long coherence length, but alternatively it may emit light in a broader bandwidth and be combined with a filter that narrows down the bandwidth to said sensing bandwidth.

It is noted that in an arrangement of the present invention the aperture of the objective lens 18 is relatively large, e.g. with an NA value larger than 0.1. A larger NA value provides for a wider opening angle and makes it possible to catch radiation from wide range angles. This is favorable for examining object samples having steep surfaces. Typically the aperture of the eyepiece lens 19 is chosen relatively small so as to match the speckle size with the size of the sensitive surface of the individual sensor element(s).

Figure 7:
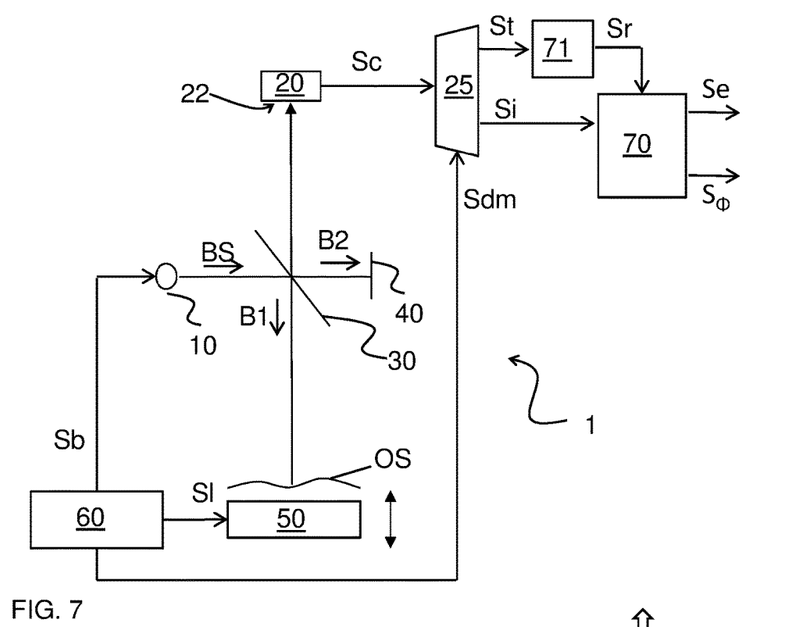
FIG. 7 shows a second embodiment of an optical coherence tomography microscopy apparatus according to the present invention.

FIG. 7 shows an alternative embodiment. Therein the photosensor arranged to sense an interference pattern for light within the sensing bandwidth is included in the photo sensor unit 20. The apparatus 1 further comprises a facility to alternate a bandwidth of the light source between the emission bandwidth and a sub-band of said emission bandwidth corresponding to the sensing bandwidth. During operation the apparatus measures a first interference when the light source is caused to emit light in the emission bandwidth and measures a second interference when the light source is caused to emit light in the sub-band of the emission bandwidth.

In this embodiment the first optical path extends from the light source 10 via the beam splitter 30 to the sample object OS via the beam splitter to photo sensor unit 20. The second optical path extends from the light source 10 via the beam splitter 30 to the reference object 40 via the beam splitter to photo sensor unit 20.

In this embodiment the third optical path fully coincides with the first optical path. The fourth optical path fully coincides with the second optical path.

During operation the controller 60 causes the light source 10 with bandwidth control signal Sb to alternately emit radiation in the emission bandwidth and in the sub-band of the emission bandwidth. The resulting interference pattern is sensed by photo-sensor unit 20 in sense region 22 and in response to thereto a composite signal Sc is generated. The controller 60 generates a demux control signal synchronous with the bandwidth control signal Sb. A demultiplexer 25, controlled by control signal Sdm, slices the composite signal Sc into a first component St that is representative for interference in narrow bandwidth range and a second signal component Si that is representative for interference in wide bandwidth range. The first signal component St is used to generate the detection reference signal Sr, which is used for detection of the envelope signal Se and the phase signal $S_\Phi$ from the second signal component Si.

Figure 8A:
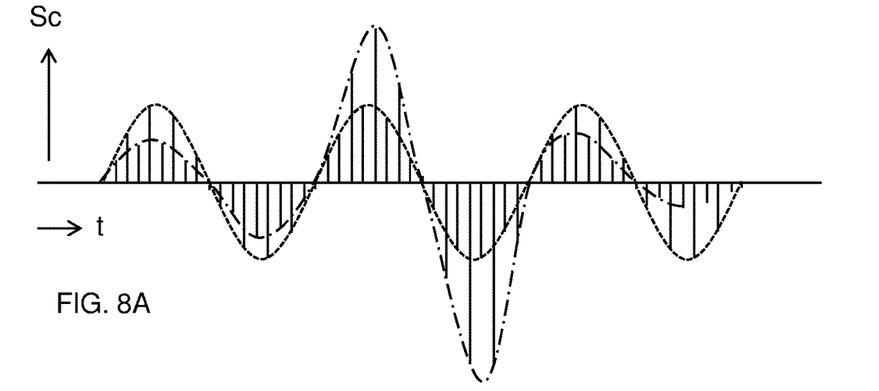
FIGS. 8A, 8B and 8C show respective signals occurring in this embodiment.
Figure 8B:
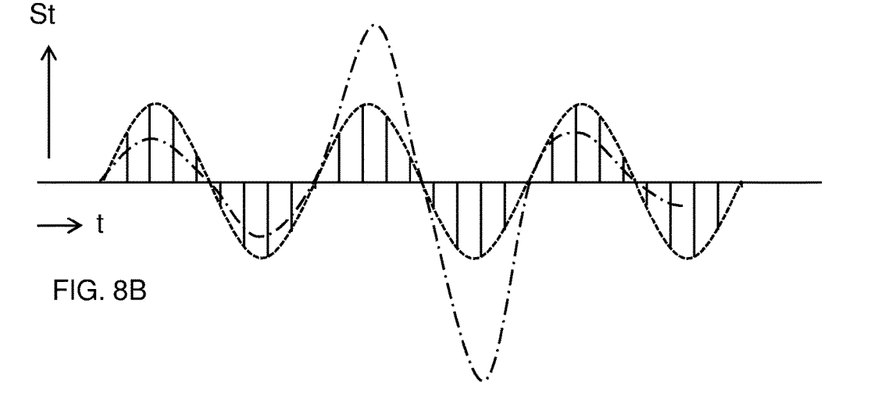
Figure 8C:
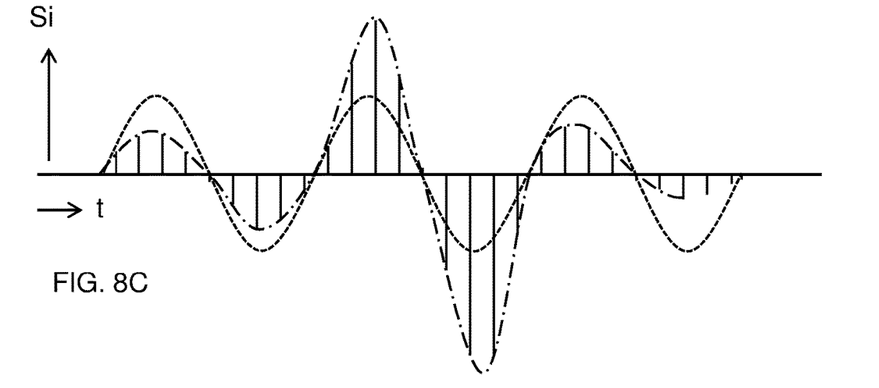

This is schematically illustrated in FIG. 8A,B,C. Therein FIG. 8A shows the composite signal Sc, comprising alternately samples from the interference pattern caused by interference in the relatively wide band width and samples from the interference pattern caused by interference in the relatively small band width.

FIG. 8B shows the first signal component St which is demultiplexed from the signal Sc and that is representative for interference in the relatively narrow bandwidth. Due to the relatively narrow bandwidth a large coherence length is obtained so that the first signal component St that is used to generate the detection reference signal Sr is available over the full scanning range.

FIG. 8C shows the second signal component Si which is demultiplexed from the signal Sc and that is representative for interference in the relatively wide bandwidth. Due to the relatively wide bandwidth a small coherence length is obtained. Therewith it can be used to generate an envelope signal Se that sharply peaks when the pathlength difference is close to 0, so that a high resolution can be obtained. As will be noted in the example shown in FIG. 6, multiple peaks may occur as a result of reflections at several levels of the sample object, for example at different layers of a partially transparent sample object.

By way of example the frequency $f_{bw}$ with which the bandwidth is controlled between the relative small and the relatively wide bandwidth is about 10 times the carrier frequency $f_c$ in the interference signals induced by the temporarily changing path length difference. In practice another bandwidth control frequency may be used provided that it is at least twice the carrier frequency.

Figure 7A:
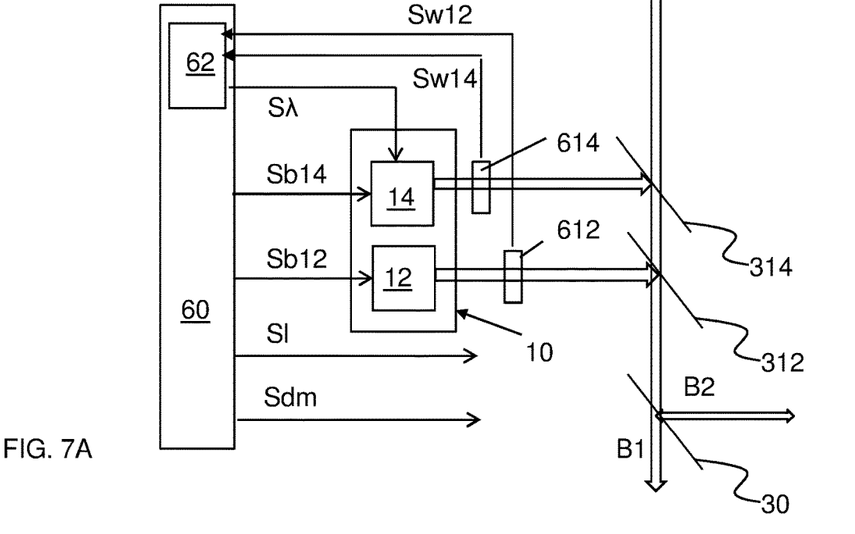
FIG. 7A shows a variation of the second embodiment.

As illustrated in FIG. 7A, the light source 10 may for example comprise a first light emitting element 12 to emit light in the emission bandwidth and a second light emitting element 14 to emit light in the sub-band of the emission bandwidth. During operation the controller 60 alternates the bandwidth the light source 10 between the emission bandwidth and the sub-band of the emission bandwidth by alternatingly activating the first light emitting element 12 with activation signal Sb12 and the second light emitting element 14 with activation signal Sb14.

In the example shown in FIG. 7A, the first light emitting element 12 is a LED. Furthermore, therein the second light emitting element 14 is a laser having a controllable central emission wavelength as a function of control signal Sλ. The facility 60 further comprises a feedback module to minimize a difference between the central emission wavelength of the laser and a central emission wavelength of the LED. The feedback module includes a sensor 612 that issues a sense signal Sw12 that is indicative for a sensed central emission wavelength of the first light emitting element 12, a sensor 614 that issues a sense signal Sw14 that is indicative for a sensed central emission wavelength of the first light emitting element 14 and a wavelength controller 62 that issues a control signal Sλ to control the central emission wavelength of the laser in response to the sense signal Sw12, Sw14 so as to minimize a difference in central emission wavelength of the first and the second light emitting element 12, 14. The central emission wavelength of the laser 14 may for example be controlled by its temperature.

In the embodiment shown in FIG. 7A the apparatus further comprises a first and a second semi-transparent mirror 312, 314 to redirect the beam emitted by the first and the second light emitting element 12, 14 towards the beam-splitter 30.

Figure 9:
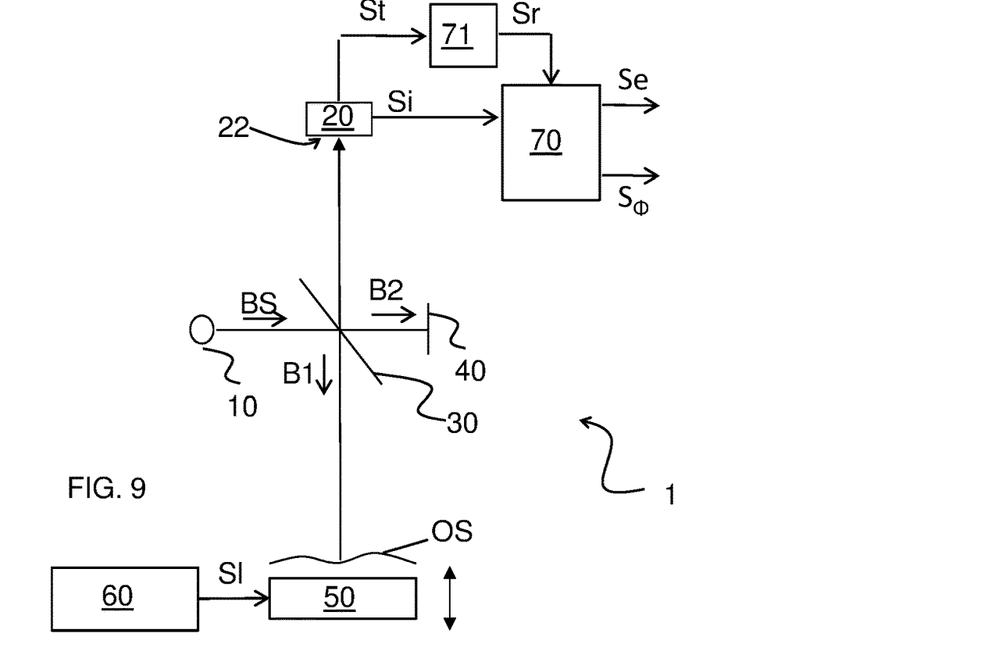
FIG. 9 shows a third embodiment of an optical coherence tomography microscopy apparatus according to the present invention.
Figure 9A:
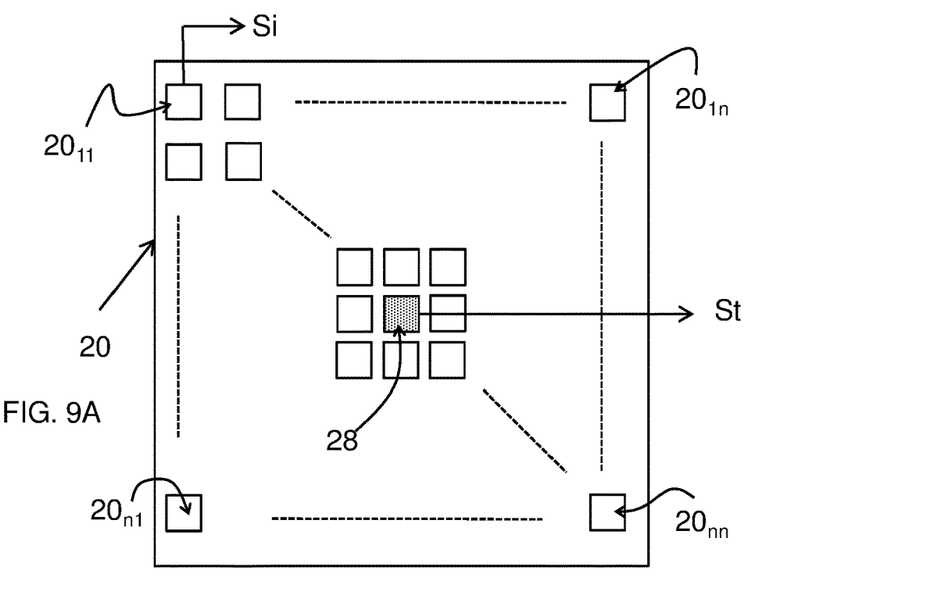
FIG. 9A shows a part of the apparatus of FIG. 9 in more detail

FIG. 9, 9A show an alternative embodiment. As shown in FIG. 9A the photo sensor unit 20 includes a plurality of sensor elements $20_{11}, \ldots, 20_{1n}, \ldots 20_{n1}, \ldots, 20_{nn}$ that are arranged in a two dimensional array. In the embodiment shown the sensor elements are arranged in a regular grid, along mutually orthogonal directions. Alternatively another type of grid may be applied, for example a hexagonal grid or a random grid. The sensor elements $20_{11}, \ldots, 20_{1n}, \ldots 20_{n1}, \ldots, 20_{nn}$ are sensitive to radiation in a large bandwidth for example coinciding with the emission bandwidth of the light source 10. In addition the photo sensor unit 20 includes one sensor element 28 that is only sensitive for light in a relatively narrow bandwidth. The sensor element 28 may be a sensor element of the same type as the sensor elements $20_{11}, \ldots, 20_{1n}, \ldots 20_{n1}, \ldots, 20_{nn}$ and additionally be provided with a band pass filter that only passes light in the relatively narrow bandwidth to that sensor element 28. Alternatively the sensor element 28 may be of a different type that can only convert light in said relatively narrow bandwidth into an electric signal.

By way of example it is shown in FIG. 9, 9A that the sense signal Si provided by the sensor element $20_{11}$ is detected with circuitry 70, 71 to generate an envelope signal Se and a phase signal $S_\Phi$. Therewith signal St from sensor element 28 is used to generate the detection reference signal Sr. In practice each of the sensor elements $20_{11}, \ldots, 20_{1n}, \ldots 20_{n1}, \ldots, 20_{nn}$ will have a respective copy of circuit 70 to generate the corresponding envelope signal Se and a phase signal $S_\Phi$. Therewith the same detection reference signal Sr can be used. It may alternatively be considered to use detection circuitry that is time-shared by a plurality of sensor elements.

In summary a method and apparatus are provided for detecting a three-dimensional image of an optically translucent or reflective object OS, with an interferometric optical setup. The method includes
   emitting a beam of light having an emission bandwidth,
   splitting the emitted beam BS into a first beam B1 a second beam B2 to be directed along respective first and second optical paths towards a sensing region. The first optical path includes the optically translucent or reflective sample object OS and the second optical path includes an optically translucent or reflective reference object.
   changing a difference between a path length of the first optical path and a path length of the second optical path,
   sensing a light intensity in the sensing region and generating a sense signal indicative for the light intensity. Therewith the sensed light intensity is modulated due to a temporarily changing interference caused by the changing difference in path length,
   demodulating the sense signal,
The sense signal is demodulating by detection using a detection reference signal that is derived from a measurement signal indicative for the actual change in the path length difference. Preferably the detection reference signal is derived by measuring a temporal change in interference in a sensing bandwidth narrower than the emission bandwidth. The interference occurs between light received along a third optical path that includes the sample object and light along a fourth optical path that includes the reference object and that originates from a common light source. The path length difference between the third and the fourth optical path changes corresponding to said changing difference between the path length of the first optical path and the path length of the second optical path. As the sensing bandwidth is relatively small, the coherence length of the light is long so that the detection reference signal is available over a long scanning depth. As the emission bandwidth is relatively large, the coherence length for imaging is short, so that a high axial resolution is achieved.

Although typically a beam-splitter may be used to split the emitted beam BS into the sub-beams B1, B2, alternatively a divergent light source may be used and mutually diverging parts of the emitted beam may be redirected as the first and second sub-beams along the sample object and the reference object.

Figure 10:
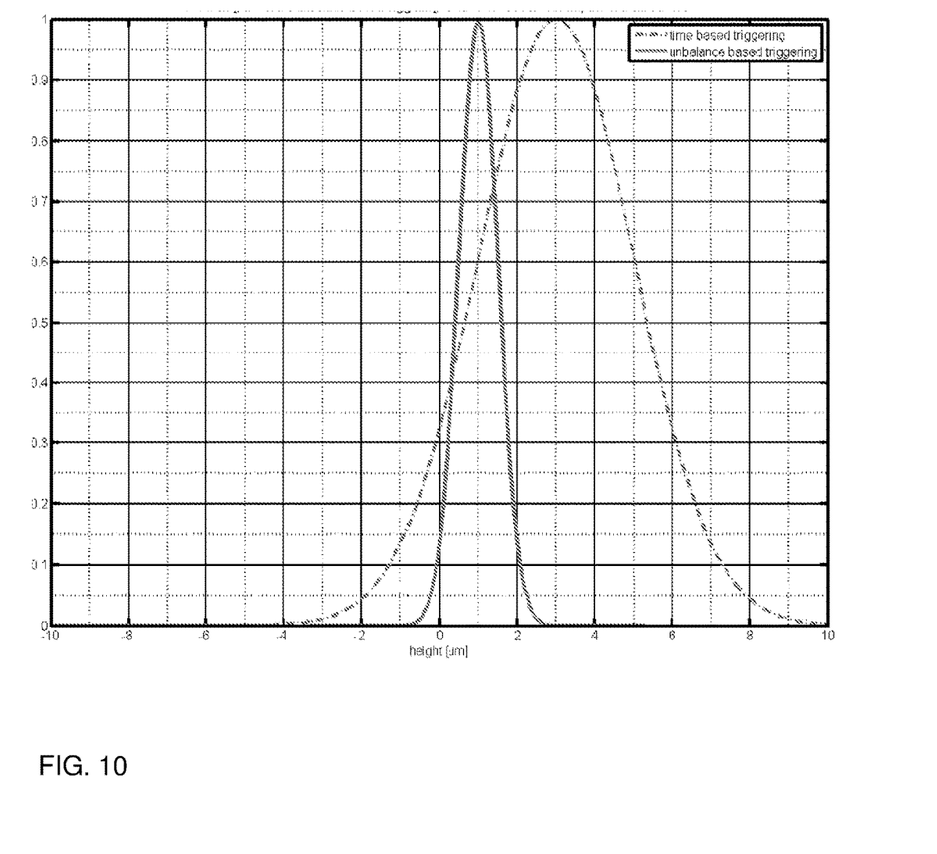
FIG. 10 shows comparison between simulation results obtained from a simulation of an embodiment of an optical coherence tomography microscopy apparatus according to the present invention and simulation results obtained from a simulation of an embodiment of an optical coherence tomography microscopy apparatus according to the prior art.

FIG. 10 shows a comparison between simulation results obtained from a simulation of an embodiment of an optical coherence tomography microscopy apparatus according to the present invention as shown in FIG. 3 and simulation results obtained from a simulation of an embodiment of an optical coherence tomography microscopy apparatus according to the prior art as shown in FIG. 1.

To that end a test object having an planarized surface at level 0 was provided as the sample object O. Simulation results obtained with a simulation of an apparatus according to the prior art are represented as the dotted curve in FIG. 10. Simulation results obtained with a simulation of an apparatus according to the present invention are represented as the solid curve therein. As can be seen the simulation results for the prior art apparatus have a systematic error of 3 micron and a standard deviation of about 3 micron. The systematic error and the standard deviation in the simulation results of the apparatus according to the present invention are both about 1 micron, and therewith substantially smaller than the systematic error and the standard deviation found for the prior art apparatus.

As will be apparent to a person skilled in the art, the elements listed in the apparatus claims are meant to include any hardware (such as separate or integrated circuits or electronic elements) or software (such as programs or parts of programs) which reproduce in operation or are designed to reproduce a specified function, be it solely or in conjunction with other functions, be it in isolation or in co-operation with other elements. The invention can be implemented by means of hardware comprising several distinct elements, and by means of a suitably programmed computer. In the apparatus claim enumerating several means, several of these means can be embodied by one and the same item of hardware.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

The invention claimed is:

1. An optical coherence tomography microscopy apparatus for detecting a three-dimensional image of an optically translucent or reflective sample object, the apparatus comprising an interferometric optical setup including:
   a light source comprising one or more light emitting elements, to emit a beam of light having an emission bandwidth, a photo sensor unit including at least one photo sensor able to sense a light intensity in a sensing region and to generate a sense signal indicative for said light intensity, the sensed light intensity being dependent on interference in said sensing region between a first and a second sub-beam impingent on the sensing region, and that are split off from said emitted beam, said first sub-beam being directed along a first optical path extending from the light source to the sensing region via the optically translucent or reflective sample object, and the second sub-beam being directed along a second optical path extending from the light source to the sensing region via the optically translucent or reflective reference object, a displacement unit to change a difference in path length between said first optical path and said second optical path, therewith causing a modulation in the sensed light intensity, a demodulator to demodulate the sense signal, characterized in that the apparatus further includes a displacement sensor to generate a displacement signal indicative for said change in said path length difference and a reference signal generator to generate a detection reference signal from the displacement signal and in that said demodulator comprises a detector using said detection reference signal.

2. An optical coherence tomography microscopy apparatus according to claim 1, wherein a reference period of the reference signal corresponds to a predetermined change in path length difference and wherein said reference period further corresponds to a fraction ½N of a period of a central wavelength of the light source, wherein N is a positive integer.

3. An optical coherence tomography microscopy apparatus according to claim 2, characterized in that a ruler-encoder type of displacement sensor is used to generate the detection reference signal.

4. The apparatus according to claim 3, wherein the reference period, of said detection reference signal generated by the ruler-encoder type of displacement sensor and corresponding to said fraction ½N of the period of the central wavelength of the light source, is obtained by said displacement meter having markings at a mutual distance.

5. The apparatus according to claim 3, wherein the ruler-encoder type of displacement sensor is arranged to provide a first output signal indicative for a sine function of a detected displacement and a second output signal indicative for a cosine function of the detected displacement, which first and second output signal in combination indicate a phase that linearly varies with the displacement, the apparatus further being provided with a linear interpolator that outputs the reference signal as a signal having a phase that is a multiplication factor times the phase of the signal indicated by the first and the second output signal, said multiplication factor being specified in accordance with the specification of the light source to provide the reference signal to sample the sense signal.

6. An optical coherence tomography microscopy apparatus according to claim 1, characterized in that the displacement sensor includes a further photo sensor to measure a temporal change in interference in a sensing bandwidth narrower than said emission bandwidth, said interference occurring between a third sub-beam being directed along a third optical path including the sample object and a fourth sub-beam directed along a fourth optical path including the reference object, said third and fourth sub-beam originating from a common light source, wherein a path length difference between the third and the fourth optical path changes corresponding to said changing difference between the path length of the first optical path and the path length of the second optical path and wherein the detection reference signal is used to sample the sense signal.

7. An optical coherence tomography microscopy apparatus according to claim 6, characterized in that the further photo sensor is sensitive only for light in the sensing bandwidth.

8. An optical coherence tomography microscopy apparatus according to claim 7, characterized in that the further photo sensor is arranged to sense an interference pattern for light within said sensing bandwidth in that a band pass filter is arranged in at least one of the third and the fourth optical paths, the band pass filter selectively passing light corresponding to said sensing bandwidth to the further photosensor.

9. An optical coherence tomography microscopy apparatus according to claim 8, further including a beam splitter arranged at a location common to the third and the fourth optical path and subsequent to a location of the sample object in said third optical path and subsequent to a location of the reference object in said fourth optical path, wherein said beam splitter splits incoming light into a fifth beam directed towards the photo sensor unit and a sixth beam directed to said further photo sensor.

10. An optical coherence tomography microscopy apparatus according to claim 6, wherein said common light source is the light source, wherein the photosensor arranged to sense an interference pattern for light within said sensing bandwidth is included in said photo sensor unit and wherein the apparatus is configured to alternate a bandwidth of said light source between said emission bandwidth and a sub-band of said emission bandwidth corresponding to said sensing bandwidth, and to measure a first interference when the light source is caused to emit light in said emission bandwidth and to measuring a second interference when the light source is caused to emit light in said sub-band of the emission bandwidth.

11. An optical coherence tomography microscopy apparatus according to claim 10, wherein said light source comprises a first light emitting element to emit light in said emission bandwidth and a second light emitting element to emit light in said sub-band of said emission bandwidth and wherein the apparatus is configured to alternate the bandwidth of said light source between said emission bandwidth and the sub-band of said emission bandwidth by alternatingly activating the first light emitting element and the second light emitting element.

12. An optical coherence tomography microscopy apparatus according to claim 11, wherein at least one of the first light emitting element and the second light emitting element has a controllable central emission wavelength, and wherein the apparatus further comprises a feedback module to minimize a difference between the central emission wavelength of the first light emitting element and the second light emitting element.

13. An optical coherence tomography microscopy apparatus according to claim 12, wherein said first light emitting element is a LED and said second light emitting element is a laser, wherein said laser has a central emission wavelength that is controllable by its temperature.

14. An optical coherence tomography microscopy apparatus according to claim 6, comprising a semitransparent mirror to split off the first and the second sub-beam from the emitted beam.

15. An optical coherence tomography microscopy apparatus according to claim 6, wherein the paths of the third and the fourth sub-beam at least substantially coincide with the paths of the first and the second sub-beam respectively.

16. An optical coherence tomography microscopy apparatus according to claim 6, wherein the paths of the third and the fourth sub-beam differ from the paths of the first and the second sub-beam.

17. An optical coherence tomography microscopy apparatus according to claim 1, wherein said detector includes a detection signal generator part that generates a first and second multiplication signal that are mutually out of phase and synchronous to the detection reference signal, and said detector further includes a first and a second multiplication unit to calculate a respective product signal by multiplying said sense signal with said first and second multiplication signal respectively, and further includes an envelop detection unit to generate the detection signal from said first and second product signal.

18. An optical coherence tomography microscopy apparatus according to claim 17, further including a phase detector for generating a phase signal from said first and second product signal.

19. An optical coherence tomography microscopy apparatus according to claim 1, wherein the light intensity is sensed by the photosensor through an objective lens having a numerical aperture of at least 0.01.

20. An optical coherence tomography microscopy apparatus according to claim 19, wherein the light intensity is further sensed by the photosensor through an eyepiece lens dimensioned to achieve a speckle size that is substantially equal to a size of the at least one photo sensor.

21. A method of detecting a three-dimensional image of an optically translucent or reflective object, with an interferometric optical setup including
emitting a beam of light having an emission bandwidth,
splitting the emitted beam into a first beam a second beam to be directed along respective first and second optical paths towards a sensing region, the first optical path including the optically translucent or reflective sample object and the second optical path including an optically translucent or reflective reference object,
changing a difference between a path length of the first optical path and a path length of the second optical path,
sensing a light intensity in said sensing region and generating a sense signal indicative for said light intensity, the sensed light intensity being modulated due to a temporarily changing interference caused by said changing difference in path length,
demodulating the sense signal,
wherein the method further includes generating a displacement signal indicative for said change in said path length difference and generating a detection reference signal from the displacement signal and in that said demodulating the sense signal comprises detection using the detection reference signal.

22. The method according to claim 21, wherein a period of the reference signal corresponds to a predetermined change in path length difference and wherein said period further corresponds to a fraction ½N of the period of a central wavelength of said emitted beam of light, wherein N is a positive integer.

23. The method according to claim 21, characterized by using a ruler-encoder type of displacement sensor to generate the detection reference signal.

24. The method according to claim 21, characterized by using a photo sensor to measure a temporal change in interference in a sensing bandwidth narrower than said emission bandwidth, said interference occurring between a third sub-beam being directed along a third optical path including the sample object and a fourth sub-beam directed along a fourth optical path including the reference object, said third and fourth sub-beam originating from a common light source, wherein a path length difference between the third and the fourth optical path changes corresponding to said changing difference between the path length of the first optical path and the path length of the second optical path and by generating the reference signal to sample the sense signal.

* * * * *